(12) United States Patent
Dunkel et al.

(10) Patent No.: US 8,026,195 B2
(45) Date of Patent: Sep. 27, 2011

(54) FUNGICIDAL N-CYCLOALKYL-CARBOXAMIDE DERIVATIVES

(75) Inventors: Ralf Dunkel, Lyons (FR); Stéphanie Gary, Champagne au Mont d'Or (FR); Marie-Claire Grosjean-Cournoyer, Curis Au Mont d'Or (FR); Philippe Rinolfi, Chatillon d'Azergues (FR); Arounarith Tuch, Lyons (FR)

(73) Assignee: Bayer Cropscience AG (DE)

( * ) Notice: Subject to any disclaimer, the term of this patent is extended or adjusted under 35 U.S.C. 154(b) by 125 days.

(21) Appl. No.: 12/309,805

(22) PCT Filed: Jul. 30, 2007

(86) PCT No.: PCT/EP2007/057836
§ 371 (c)(1),
(2), (4) Date: Apr. 1, 2009

(87) PCT Pub. No.: WO2008/015189
PCT Pub. Date: Feb. 7, 2008

(65) Prior Publication Data
US 2009/0326016 A1 Dec. 31, 2009

(30) Foreign Application Priority Data
Jul. 31, 2006 (EP) .................................... 06356098

(51) Int. Cl.
*A01N 43/00* (2006.01)
*C07D 231/00* (2006.01)
(52) U.S. Cl. .................. 504/139; 548/374.1; 548/375.1
(58) Field of Classification Search ............... 548/374.1, 548/375.1; 504/139
See application file for complete search history.

(56) References Cited

FOREIGN PATENT DOCUMENTS
WO WO 01/55124 8/2001
WO WO 2007/029035 3/2007

OTHER PUBLICATIONS

Sugiura et. al., CAS STN English abstract, 1990, CAS.*
Kuzuya et. al., Journal of Experimental Biology, 2003, Society for Experimental Biology, vol. 54, No. 384, pp. 1069-1074.*
Database Registry [Online] Chemical Abstracts Service, Columbus, Ohio, US; Apr. 4, 2006, XP002429737 . retrieved from STN CAS Registry No. 879146-75-5 abstract.
Database Registry [Online] Chemical Abstracts Service, Columbus, Ohio, US; Aug. 12, 2005, XP002429738 retrieved from STN CAS Registry No. 859872-65-4 abstract.
Database Registry [Online] Chemical Abstracts Service, Columbus, Ohio, US; Aug. 11, 2005, XP002429739 retrieved from STN CAS Registry No. 859651-09-5 abstract.
Database Registry [Online] Chemical Abstracts Service, Columbus, Ohio, US; Aug. 5, 2005, XP002429740 retrieved from STN CAS Registry No. 858547-51-0 abstract.
Database Registry [Online] Chemical Abstracts Service, Columbus, Ohio, US; Aug. 3, 2005, XP002429741 retrieved from STN CAS Registry No. 858113-86-7 abstract.
Database Registry [Online] Chemical Abstracts Service, Columbus, Ohio, US; Jul. 11, 2005, XP002429742 retrieved from STN CAS Registry No. 854542-46-4 abstract.
Database Registry [Online] Chemical Abstracts Service, Columbus, Ohio, US; Jun. 29, 2005, XP002429743 retrieved from STN CAS Registry No. 853252-77-4 abstract.
Database Registry [Online] Chemical Abstracts Service, Columbus, Ohio, US; Nov. 30, 2004, XP002429744 retrieved from STN CAS Registry No. 790718-64-8 abstract.

* cited by examiner

*Primary Examiner* — Sreeni Padmanabhan
*Assistant Examiner* — Sarah Pihonak
(74) *Attorney, Agent, or Firm* — Ostrolenk Faber LLP

(57) ABSTRACT

The present invention relates to N-cycloalkyl-thiocarboxamide or N-cycloalkyl-N-substituted carboximidamide derivatives of formula (I) wherein A and B represent a 5-membered heterocyclyl groups, T represents an oxygen, sulphur or amino derivatives, $Z^1$ represents a cycloalkyl group and $Z^2$ and $Z^3$ represent various substituents, their process of preparation, their use as fungicide active agents, particularly in the form of fungicide compositions, and methods for the control of phytopathogenic fungi, notably of plants, using these compounds or compositions.

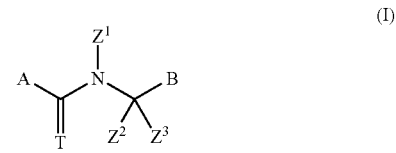

(I)

12 Claims, No Drawings

FUNGICIDAL N-CYCLOALKYL-CARBOXAMIDE DERIVATIVES

The present application is a 35 U.S.C. §371 national phase conversion of International Application No. PCT/EP2007/057836 filed Jul. 30, 2007, which claims priority of European Application No. 06356098.1 filed Jul. 31, 2006.

The present invention relates to N-cycloalkyl-thiocarboxamide or N-cycloalkyl-N-substituted carboximidamide derivatives, their process of preparation, their use as fungicide active agents, particularly in the form of fungicide compositions, and methods for the control of phytopathogenic fungi, notably of plants, using these compounds or compositions.

In international patent application WO-2001/55124, there are generically embraced certain isothiazolecarboxylic acid derivatives of the following formula:

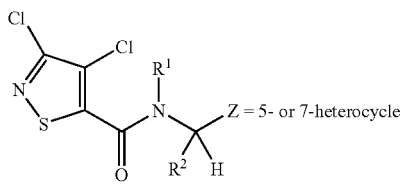

wherein $R^1$ can represent a $C_3$-$C_6$-cycloalkyl and $R^2$ can represent various substituents. However, this document does not disclose any such compounds nor it provides any biological activity thereon.

In international patent application WO-96/38419 certain 2-pyridyl-methylene-carboxamide and thiocarboxamide derivatives are generically embraced in a broad disclosure of numerous compounds of the following formula:

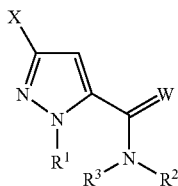

wherein X represents halogen, W can represent an oxygen or a sulphur atom, $R^1$ can represent $C_1$-$C_4$-alkyl, $R^2$ can represent $C_3$-$C_7$-cycloalkyl and $R^3$ can represent various substituents such as heterocycles. However, this document does not specifically disclose nor suggest to select such compounds wherein the nitrogen atom of the carboxamide or thiocarboxamide residue can be substituted by a cycloalkyl.

In international patent application WO-2006/098128 certain 2-pyridyl-methylene-carboxamide and thiocarboxamide derivatives are generically embraced in a broad disclosure of numerous compounds of the following formula:

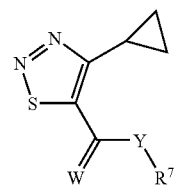

wherein W can represent an oxygen or a sulphur atom, Y can represent N-cycloalkyl and $R^7$ can represent various substituents such as heterocycles. However, this document does not specifically disclose nor suggest to select such compounds wherein the nitrogen atom of the carboxamide or thiocarboxamide residue might be substituted by a cycloalkyl.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds that possess the above mentioned effects or advantages.

Accordingly, the present invention provides N-cycloalkyl-carboxamide derivatives of formula (I)

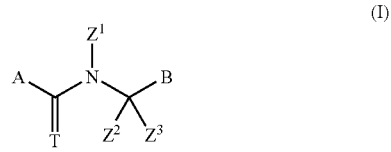

wherein
A represents a carbo-linked, unsaturated, 5-membered heterocyclyl group that can be substituted by up to four groups R;
B represents a carbo-linked, unsaturated, 5-membered heterocyclyl group that can be substituted by up to four groups X;
T represents O, S, $NR^a$, $NOR^a$, $NNR^aR^b$ or N—CN;
$R^a$ and $R^b$, that can be the same or different, represent a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; phenylsulphonyl that can be substituted by up to 5 groups Q
$Z^1$ represents a non substituted $C_3$-$C_7$-cycloalkyl or a $C_3$-$C_7$ cycloalkyl substituted by up to 10 atoms or groups that can be the same or different and that can be selected in the list consisting of a halogen atoms; cyano; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different;

$Z^2$ and $Z^3$, that can independently be the same or different, represent a hydrogen atom a halogen atom; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-alkynyl; cyano; nitro; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-$C_1$-$C_8$-alkylamino; $C_1$-$C_8$-alkoxycarbonyl; $C_1$-$C_8$-alkylcarbonyl; $C_1$-$C_8$-alkylcarbamoyl di-$C_1$-$C_8$-alkylcarbamoyl; N—$C_1$-$C_8$-alkyl-$C_1$-$C_8$-alkoxycarbamoyl; or $Z^2$ and $Z^3$ together with the carbon atom to that they are linked can form a substituted or non substituted $C_3$-$C_7$ cycloalkyl;

R, that can be the same or different, represent a hydrogen atom; a halogen atom; cyano; nitro; amino; sulfanyl; hydroxyl; pentafluoro-$\lambda$-6-sulfanyl; $C_1$-$C_8$-alkylamino; di-$C_1$-$C_8$-alkylamino; tri($C_1$-$C_8$-alkyl)silyl; tri($C_1$-$C_8$-alkyl)silyl-$C_1$-$C_8$-alkyl; $C_1$-$C_8$-alkylsulfanyl; $C_1$-$C_8$-halogenoalkylsulfanyl comprising up to 9 halogen atoms that can be the same or different; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_1$-$C_8$-alkoxy; $C_1$-$C_8$-alkoxy-$C_1$-$C_8$-alkyl; $C_1$-$C_8$-halogenoalkoxy comprising up to 9 halogen atoms that can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$alkylsulphinyl; $C_1$-$C_8$-alkylsulphonyl; $C_1$-$C_8$alkoxyimino; ($C_1$-$C_8$-alkoxyimino)-$C_1$-$C_8$-alkyl; (benzyloxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-$C_1$-$C_8$-alkylaminocarbonyl;

X, that can be the same or different, represents a hydrogen atom; a halogen atom; nitro; cyano; hydroxyl; sulphanyl; amino; pentafluoro-$\lambda$6-sulphanyl; $C_1$-$C_8$-alkyl; $C_1$-$C_8$-halogenoalkyl comprising up to 9 halogen atoms that can be the same or different; $C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_1$-$C_8$-alkylsulphanyl; $C_1$-$C_8$-halogenoalkylsulphanyl comprising up to 9 halogen atoms that can be the same or different; $C_1$-$C_8$-alkylsulphenyl, $C_1$-$C_8$-halogenoalkylsulphenyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogenoalkyl-sulphonyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different $C_2$-$C_8$-alkenyloxy; $C_2$-$C_8$-halogenoalkenyloxy comprising up to 9 halogen atoms that can be the same or different; $C_2$-$C_8$-alkinyloxy; $C_2$-$C_8$-halogenoalkinyloxy comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; N—$C_1$-$C_8$-alkyl-$C_1$-$C_8$-alkoxycarbamoyl; $C_1$-$C_8$-alkylcarbonyloxy; $C_1$-$C_8$-halogenoalkylcarbonyloxy comprising up to 9 halogen atoms that can be the same or different; $C_1$-$C_8$-alkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkoxyimino; ($C_1$-$C_8$-alkoxyimino)-$C_1$-$C_8$-alkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; phenyl that can be substituted by up to 5 groups Q; benzyloxy that can be substituted by up to 5 groups Q; benzylsulphanyl that can be substituted by up to 5 groups Q; benzylamino that can be substituted by up to 5 groups Q; phenoxy that can be substituted by up to 5 groups Q; phenylamino that can be substituted by up to 5 groups Q; phenylsulphanyl that can be substituted by up to 5 groups Q; benzyl that can be substituted by up to 5 groups Q; pyridinyl that can be substituted by up to four groups Q and pyridinyloxy that can be substituted by up to four groups Q;

Q, that can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; ($C_1$-$C_8$-alkoxyimino)-$C_1$-$C_8$-alkyl;

as well as salts, N-oxides, metallic complexes, metalloidic complexes and optically active or geometric isomers thereof.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods that are known per se by the man ordinary skilled in the art.

According to the invention, the following generic terms are generally used with the following meanings:
  halogen means fluorine, chlorine, bromine or iodine;
  heteroatom can be nitrogen, oxygen or sulphur;
  halogenated groups, notably haloalkyl, haloalkoxy and cycloalkyl groups, can comprise up to nine identical or different a halogen atoms;
  any alkyl, alkenyl or alkynyl group can be linear or branched;
  the term "aryl" means phenyl or naphthyl, optionally substituted by one to five groups selected in the list consisting of halogen, [$C_1$-$C_6$]-alkyl, [$C_1$-$C_6$]-haloalkyl, [$C_2$-$C_6$]-alkenyl, [$C_2$-$C_6$]-haloalkenyl, [$C_2$-$C_6$]-alkynyl, [$C_2$-$C_6$]-haloalkynyl, [$C_1$-$C_6$]-alkoxy, [$C_1$-$C_4$]-alkoxy-[$C_1$-$C_4$]-alkyl, [$C_1$-$C_4$]-alkoxy-[$C_1$-$C_4$]-alkoxy, [$C_1$-$C_6$]-haloalkoxy and [$C_1$-$C_4$]-haloalkoxy-[$C_1$-$C_4$]-alkyl;
  in the case of an amino group or the amino moiety of any other amino-containing group, substituted by two substituents that can be the same or different, the two substituents together with the nitrogen atom to that they are linked can form a heterocyclyl group, preferably a 5- to 7-membered heterocyclyl group, that can be substituted or that can include other hetero atoms, for example a morpholino group or piperidinyl.

Preferred compounds of formula (I) according to the invention are those wherein A is selected in the list consisting of:

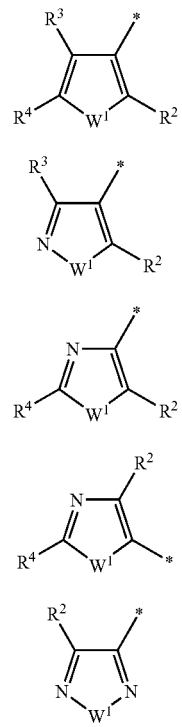

wherein:
- -* represents the bond to the carbonyl group;
- $W^1$ represents O, S or $NR^1$;
- $R^1$ represents a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl;
- $R^2$ and $R^3$, that can be the same or different represent a hydrogen atom; a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl;
- $R^4$ represents a hydrogen atom, a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl.

More preferred compounds of formula (I) according to the invention are those wherein A is selected in the list consisting of:

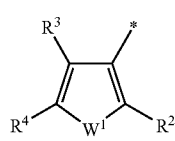

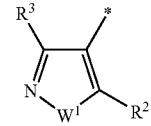

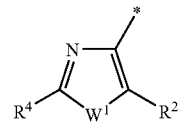

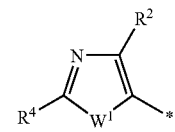

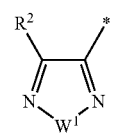

wherein:
- -* represents the bond to the carbonyl group;
- $W^1$ represents O, S or $NR^1$;
- $R^1$ represents a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl;
- $R^2$ and $R^3$, that can be the same or different represent a hydrogen atom; a halogen atom; $C_1$-$C_8$-alkyl; $C_1$-$C_8$-halogenoalkyl comprising up to 9 halogen atoms that can be the same or different;
- $R^4$ represents a hydrogen atom, a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl.

Even more preferred compounds of formula (I) according to the invention are those wherein
- A represents $A^2$;
- $W^1$ represents $NR^1$;
- $R^1$ represents $C_1$-$C_8$-alkyl;
- $R^2$ and $R^3$, that can be the same or different represent a hydrogen atom; a halogen atom; $C_1$-$C_8$-alkyl; $C_1$-$C_8$-halogenoalkyl comprising up to 9 halogen atoms that can be the same or different.

Other preferred compounds of formula (I) according to the invention are those wherein B is selected in the list consisting of:

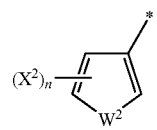

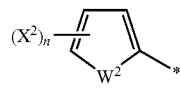

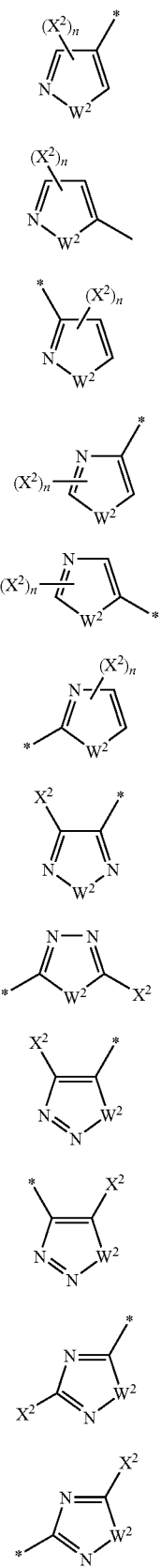

wherein:
-* represents the bond to the methylene group;

$W^2$ represents O, S or $NX^1$;

$X^1$ represents a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl;

$X^2$, that can be the same or different, represents a hydrogen atom; a halogen atom cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$cycloalkyl; phenyl that can be substituted by up to 5 groups Q; phenoxy that can be substituted by up to 5 groups Q benzyl that can be substituted by up to 5 groups Q; $C_1$-$C_8$-alkoxyimino; ($C_1$-$C_8$-alkoxyimino)-$C_1$-$C_8$-alkyl;

n=1, 2 or 3.

Other preferred compounds of formula (I) according to the invention are those wherein T represents O or S.

Other preferred compounds of formula (I) according to the invention are those wherein $Z^1$ represents cyclopropyl.

Other preferred compounds of formula (I) according to the invention are those wherein $Z^2$ and $Z^3$ independently represent a hydrogen atom or $C_1$-$C_8$ alkyl.

The above mentioned preferences with regard to the substituents of the compounds of formula (I) according to the invention can be combined in various manners, either individually, partially or entirely. These combinations of preferred features thus provide sub-classes of compounds according to the invention. Examples of such subclasses of preferred compounds according to the invention can combine:

preferred features of A with preferred features of one or more of T, $Z^1$, $Z^2$, $Z^3$ and B;

preferred features of T with preferred features of one or more of A, $Z^1$, $Z^2$, $Z^3$ and B preferred features of $Z^1$ with preferred features of one or more of A, T, $Z^2$, $Z^3$ and B;

preferred features of $Z^2$ with preferred features of one or more of A, T, $Z^1$, $Z^3$ and B;

preferred features of $Z^3$ with preferred features of one or more of A, T, $Z^1$, $Z^2$ and B;

preferred features of B with preferred features of one or more of A, T, $Z^1$, $Z^2$ and $Z^3$.

In these combinations of preferred features of the substituents of the compounds according to the invention, the said preferred features can also be selected among the more preferred features of each of A, T, $Z^1$, $Z^2$, $Z^3$ and B; so as to form most preferred subclasses of compounds according to the invention.

The preferred features of the other substituents of the compounds according to the invention can also be part of such sub-classes of preferred compounds according to the invention, notably the groups of substituents R, X, Q, $W^1$ and $W^2$, $R^1$ to $R^4$, $X^1$ and $X^2$ as well as the integer n.

The present invention also relates to a process for the preparation of a compound of formula (I) wherein T represents O. Thus according to a further aspect of the present invention, there is provided a process P1 for the preparation of a compound of formula (I) as herein-defined, as illustrated by the following reaction scheme:

Process P1

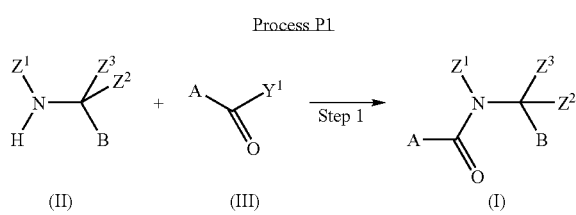

wherein

A, B, $Z^1$ to $Z^3$ are as herein-defined;

$Y^1$ represents a halogen atom or a hydroxyl group.

In process P1 according to the invention, step 1 can be performed if appropriate in the presence of a solvent and if appropriate in the presence of an acid binder.

N-cycloalkyl-amine derivatives of formula (II) are known or can be prepared by known processes (J. Het. Chem., 1983, p 1031-6; J. Am. Chem. Soc., 2004, p 5192-5201; Synt. Comm. 2003, p 3419-25).

Carboxylic acid derivatives of formula (III) are known or can be prepared by known processes (WO-93/11117; EP-A 0 545 099; Nucleosides & Nucleotides, 1987, p 737-759, Bioorg. Med. Chem., 2002, p 2105-2108).

Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetate, and also ternary amines, such as trimethylamine, triethylamine, diisopropylethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). It is also possible to work in the absence of an additional condensing agent or to employ an excess of the amine component, so that it simultaneously acts as acid binder agent.

Suitable solvents for carrying out process P1 according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out process P1 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use micro-wave technology.

Process P1 according to the invention is generally carried out under atmospheric pressure. However, in each case, it is also possible to operate under elevated or reduced pressure.

When carrying out step 1 of process P1 according to the invention, generally 1 mol or other an excess of the acid derivative of formula (III) and from 1 to 3 mol of acid binder are employed per mole of amine of formula (II). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

According to a further aspect of the present invention, there is provided another process P2 for the preparation of a compound of formula (I) as herein-defined wherein T represents S, as illustrated by the following reaction scheme:

Process P2

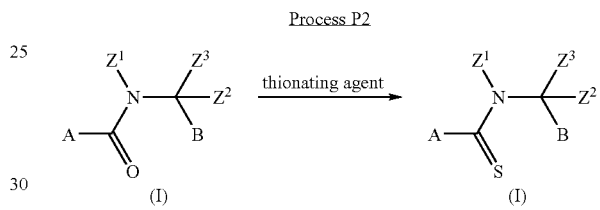

wherein

A, B, $Z^1$ t to $Z^3$ are as herein-defined.

Process P2 can be performed in the presence of a thionating agent. Amide derivatives of formula (I) wherein T represents O can be prepared according to process P1.

Suitable thionating agents for carrying out process P2 according to the invention can be sulfur (S), sulfhydric acid ($H_2S$), sodium sulfide ($Na_2S$), sodium hydrosulfide (NaHS), boron trisulfide ($B_2S_3$), bis-(diethylaluminium) sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358 in the presence or not of a catalytic, stoechiometric or more amount of a base such as an inorganic or organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methylpiperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane or 1,2-diethoxyethane; nitriles, such as acetonitrile, propionitrile, n- or i-butyronitrile or benzonitrile; sulphurous solvents, such as sulpholane or carbon disulfide.

When carrying out process P2 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Process P2 according to the invention is generally carried out under atmospheric pressure. It is also possible to operate under elevated or reduced pressure.

When carrying out process P2 according to the invention, 1 mole or an excess of the sulphur equivalent of the thionating agent and from 1 to 3 moles of the base can be employed per mole of the amide derivative of formula (I).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

According to a further aspect according to the invention, there is provided a process P3 for the preparation of compound of formula (I) as herein-defined wherein T represents $N-R^a$, $N-OR^a$, $N-NR^aR^b$ or $N-CN$ as illustrated according to the following reaction scheme:

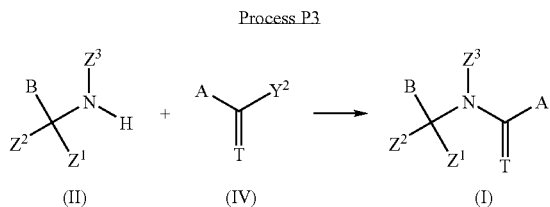

Process P3 wherein
A, $Z^1$ to $Z^3$ and B are as herein-defined;
$Y^2$ represents a chlorine atom.

Process P3 can be performed in the presence of an acid binder or in the presence of a solvent.

N-cycloalkyl-amine derivatives of formula (II) are known or can be prepared by known processes (J. Het. Chem., 1983, p 1031-6 J. Am. Chem. Soc., 2004, p 5192-5201; Synt. Comm. 2003, p 3419-25).

N-substituted carboximidoyl chloride derivative of formula (IV) are known or can be prepared by known processes, for example as described in Houben-Weyl, "Methoden der organischen Chemie" (1985), E5/1, 628-633 and Patai, "The chemistry of amidines and imidates" (1975), 296-301.

Suitable acid binders for carrying out process P3 according to the invention can be inorganic or organic bases that are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; alkaline earth metal or alkali metal hydrides, such as sodium hydride or potassium hydride; alkaline earth metal or alkali metal alcoolates, such as sodium methylate, sodium ethylate, sodium propylate or potassium t-butylate; and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU) or a polymer-supported acid scavenger (for example as detailed in http://www.iris-biotech.de/downloads/scavengers.pdf).

It is however possible to work in the absence of any additional acid binder.

Suitable solvents for carrying out process P3 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out process P3 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Process P3 according to the invention is generally carried out under atmospheric pressure. It is also possible to operate under elevated or reduced pressure.

When carrying out process P3 according to the invention, the amine derivative of formula (II) can be employed as its salt, such as chlorhydrate or any other convenient salt.

When carrying out process P3 according to the invention, 1 mole or an excess of the amine derivative of formula (II) and from 1 to 3 moles of the acid binder can be employed per mole of the N-substituted carboximidoyl chloride derivative of formula (IV).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesized.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops, and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

B1) a compound capable to inhibit the nucleic acid synthesis like benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

B2) a compound capable to inhibit the mitosis and cell division like benomyl, carbendazim, diethofencarb, ethaboxam, fuberidazole, pencycuron, thiabendazole, thiophanate-methyl, zoxamide;

B3) a compound capable to inhibit the respiration for example
   as CI-respiration inhibitor like diflumetorim;
   as CII-respiration inhibitor like boscalid, carboxin, fenfuram, flutolanil, furametpyr, furmecyclox, mepronil, oxycarboxin, penthiopyrad, thifluzamide;
   as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

B4) a compound capable of to act as an uncoupler like dinocap, fluazinam, meptyidinocap;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

B9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

B10) a compound capable to inhibit cell wall synthesis like benthiavalicarb, dimethomorph, flumorph, iprovalicarb, mandipropamid, polyoxins, polyoxorim, validamycin A;

B11) a compound capable to inhibit melanine biosynthesis like carpropamid, diclocymet, fenoxanil, phthalide, pyroquilon, tricyclazole;

B12) a compound capable to induce a host defence like acibenzolar-S-methyl, probenazole, tiadinil;

B13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations including calcium polysulphide, thiram, tolylfluanid, zineb, ziram;

B14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy-}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 1-methyl-N-[2-(1,1,2,2-tetrafluoroethoxy)phenyl]-3-trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3-(difluoromethyl)-1-methyl-N-[2-(1,1,2,2-tetrafluoroethoxy)phenyl]-1H-pyrazole-4-carboxamide, 3-(difluoromethyl)-N-[(9R)-9-isopropyl-1,2,3,4-tetrahydro-1,4-methanonaphthalen-5-yl]-1-methyl-1H-pyrazole-4-carboxamide, 3-(difluoromethyl)-N-[(9S)-9-isopropyl-1,2,3,4-tetrahydro-1,4-methanonaphthalen-5-yl]-1-methyl-1H-pyrazole-4-carboxamide, 3-(difluoromethyl)-N-[4'-(3,3-dimethylbut-1-yn-1-yl)biphenyl-2-yl]-1-methyl-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-chloro-7-(4-methylpiperidin-1-yl)-6-(2,4,6-trifluorophenyl)[1,2,4]triazolo[1,5-a]pyrimidine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluorobiphenyl-2-yl)-3-difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyrdin-2-yl)ethyl]-2-fluoro-4-iodonicotinamide, N-[2-(1,3-dimethylbutyl)phenyl]-5-fluoro-1,3-dimethyl-1H-pyrazole-4-carboxamide, N-{(Z)-[(cyclopropylmethoxy)imino][6-(difluoromethoxy)-2,3-difluorophenyl]methyl}-2-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-{2-[3-chloro-5-(trifluoromethyl)pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, S-allyl-5-amino-2-isopropyl-4-(2-methylphenyl)-3-oxo-2,3-dihydro-1H-pyrazole-1-carbothioate, tecloftalam, tecnazene, triazoxide, trichlamide, valiphenal, zarilamid.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention can be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae Sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asferaceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots) horticultural and forest crops; as well as genetically modified homologues of these crops.

Among the diseases of plants or crops that can be controlled by the method according to the invention, mention can be made of:

Powdery mildew diseases such as:
*Blumeria* diseases, caused for example by *Blumeria graminis*;
*Podosphaera* diseases, caused for example by *Podosphaera leucotricha*;
*Sphaerotheca* diseases, caused for example by *Sphaerotheca fuliginea*;
*Uncinula* diseases, caused for example by *Uncinula necator*;

Rust diseases such as:
*Gymnosporangium* diseases, caused for example by *Gymnosporangium sabinae*;
*Hemileia* diseases, caused for example by *Hemileia vastatrix*;
*Phakopsora* diseases, caused for example by *Phakopsora pachyrhizi* or *Phakopsora meibomiae*;
*Puccinia* diseases, caused for example by *Puccinia recondita*;
*Uromyces* diseases, caused for example by *Uromyces appendiculatus*;

Oomycete diseases such as:
*Bremia* diseases, caused for example by *Bremia lactucae*;
*Peronospora* diseases, caused for example by *Peronospora pisi* or *P. brassicae*;
*Phytophthora* diseases, caused for example by *Phytophthora infestans*;
*Plasmopara* diseases, caused for example by *Plasmopara viticola*;
*Pseudoperonospora* diseases, caused for example by *Pseudoperonospora humuli* or *Pseudoperonospora cubensis*;
*Pythium* diseases, caused for example by *Pythium ultimum*;

Leafspot, leaf blotch and leaf blight diseases such as:
*Alternaria* diseases, caused for example by *Alternaria solani*;
*Cercospora* diseases, caused for example by *Cercospora beticola*;
*Cladiosporum* diseases, caused for example by *Cladiosporium cucumerinum*;
*Cochliobolus* diseases, caused for example by *Cochliobolus sativus*;
*Colletotrichum* diseases, caused for example by *Colletotrichum lindemuthanium*;
*Cycloconium* diseases, caused for example by *Cycloconium oleaginum*;
*Diaporthe* diseases, caused for example by *Diaporthe citri*;
*Elsinoe* diseases, caused for example by *Elsinoe fawcettii*;
*Gloeosporium* diseases, caused for example by *Gloeosporium laeticolor*;
*Glomerella* diseases, caused for example by *Glomerella cingulata*;
*Guignardia* diseases, caused for example by *Guignardia bidwelli*;
*Leptosphaeria* diseases, caused for example by *Leptosphaeria maculans*; *Leptosphaeria nodorum*;
*Magnaporthe* diseases, caused for example by *Magnaporthe grisea*;
*Mycosphaerella* diseases, caused for example by *Mycosphaerella graminicola*; *Mycosphaerella arachidicola*; *Mycosphaerella fijiensis*;
*Phaeosphaeria* diseases, caused for example by *Phaeosphaeria nodorum*;
*Pyrenophora* diseases, caused for example by *Pyrenophora teres*;
*Ramularia* diseases, caused for example by *Ramularia collo-cygni*;
*Rhynchosporium* diseases, caused for example by *Rhynchosporium secalis*;
*Septoria* diseases, caused for example by *Septoria apii* or *Septoria lycopercisi*;
*Typhula* diseases, caused for example by *Typhula incamata*;
*Venturia* diseases, caused for example by *Venturia inaequalis*;

Root and stem diseases such as
*Corticium* diseases, caused for example by *Corticium graminearum*;
*Fusarium* diseases, caused for example by *Fusarium oxysporum*;
*Gaeumannomyces* diseases, caused for example by *Gaeumannomyces graminis*;
*Rhizoctonia* diseases, caused for example by *Rhizoctonia solani*;
*Tapesia* diseases, caused for example by *Tapesia acuformis*;
*Thielaviopsis* diseases, caused for example by *Thielaviopsis basicola*;

Ear and panicle diseases such as:
*Alternaria* diseases, caused for example by *Alternaria* spp.;
*Aspergillus* diseases, caused for example by *Aspergillus flavus*;
*Cladosporium* diseases, caused for example by *Cladosporium* spp.;
*Claviceps* diseases, caused for example by *Claviceps purpurea*;
*Fusarium* diseases, caused for example by *Fusarium culmorum*;
*Gibberella* diseases, caused for example by *Gibberella zeae*;
*Monographella* diseases, caused for example by *Monographella nivalis*;

Smut and bunt diseases such as:
*Sphacelotheca* diseases, caused for example by *Sphacelotheca reiliana*;
*Tilletia* diseases, caused for example by *Tilletia caries*;
*Urocystis* diseases, caused for example by *Urocystis occulta*;
*Ustilago* diseases, caused for example by *Ustilago nuda*;

Fruit rot and mould diseases such as:
*Aspergillus* diseases, caused for example by *Aspergillus flavus*;
*Botrytis* diseases, caused for example by *Botrytis cinerea*;
*Penicillium* diseases, caused for example by *Penicillium expansum*;
*Sclerotinia* diseases, caused for example by *Sclerotinia sclerotiorum*;
*Verticilium* diseases, caused for example by *Verticilium alboatrum*;

Seed and soilborne decay, mould, wilt, rot and damping-off diseases such as:

Fusarium diseases, caused for example by *Fusarium culmorum;*
Phytophthora diseases, caused for example by *Phytophthora cactorum;*
Pythium diseases, caused for example by *Pythium ultimum;*
Rhizoctonia diseases, caused for example by *Rhizoctonia solani;*
Sclerotium diseases, caused for example by *Sclerotium rolfsii;*
Microdochium diseases, caused for example by *Microdochium nivale;*
Canker, broom and dieback diseases such as:
Nectria diseases, caused for example by *Nectria galligena;*
Blight diseases such as:
Monilinia diseases, caused for example by *Monilinia laxa;*
Leaf blister or leaf curl diseases such as:
Taphrina diseases, caused for example by *Taphrina deformans;*
Decline diseases of wooden plants such as:
Esca diseases, caused for example by *Phaemoniella clamydospora;*
Eutypa dyeback, caused for example by *Eutypa lata;*
Dutch elm disease, caused for example by *Ceratocystsc ulmi;*
Diseases of flowers and Seeds such as:
Botrytis diseases, caused for example by *Botrytis cinerea;*
Diseases of tubers such as:
Rhizoctonia diseases, caused for example by *Rhizoctonia solani;*
Helminthosporium diseases, caused for example by *Helminthosporium solani.*

The fungicide composition according to the invention can also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention can also be used in the treatment of genetically modified organisms with the compounds according to the invention or the agrochemical compositions according to the invention. Genetically modified plants are plants into genome of that a heterologous gene encoding a protein of interest has been stably integrated. The expression "heterologous gene encoding a protein of interest" essentially means genes that give the transformed plant new agronomic properties, or genes for improving the agronomic quality of the modified plant.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus.*

The various aspects of the invention will now be illustrated with reference to the following table of compound examples and the following preparation or efficacy examples.

The following table illustrates in a non-limiting manner examples of compounds according to the invention.

In the following table, M+H (or M−H) means the molecular ion peak, plus or minus 1 a.m.u. (atomic mass unit) respectively, as observed in mass spectroscopy and M (Apcl+) means the molecular ion peak as it was found via positive atmospheric pressure chemical ionisation in mass spectroscopy.

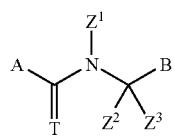

| Example N° | A | B | Z1 | T | Z2 | Z3 | M + 1 |
|---|---|---|---|---|---|---|---|
| 1 | | | | cyclopropyl | O | H | H | 458 |

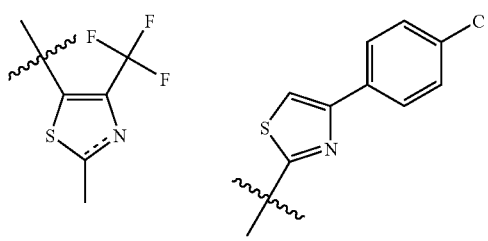

-continued
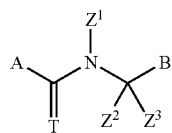
| Example N° | A | B | Z1 | T | Z2 | Z3 | M + 1 |
|---|---|---|---|---|---|---|---|
| 2 | (CF3-thiazole) | (N-methylimidazole) | cyclopropyl | O | H | H | 345 |
| 3 | (CF3-thiazole) | (oxadiazole) | cyclopropyl | O | H | H | 333 |
| 4 | (CF3-oxazole) | (thiazole) | cyclopropyl | O | H | H | 348 |
| 5 | (CF3-thiazole) | (dimethylisoxazole) | cyclopropyl | O | H | H | |
| 6 | (CF3-thiazole) | (phenyl-oxadiazole) | cyclopropyl | O | Me | H | |
| 7 | (CF3-thiazole) | (Cl-thiadiazole) | cyclopropyl | O | H | H | |
| 8 | (CF3-thiazole) | (CF3-thiazole) | cyclopropyl | O | H | H | |

-continued

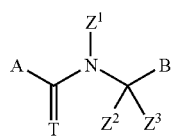

| Example N° | A | B | Z1 | T | Z2 | Z3 | M + 1 |
|---|---|---|---|---|---|---|---|
| 9 | (thiadiazole with CF3 and methyl) | (2-chloro thiazole) | cyclopropyl | O | Me | H | |
| 10 | (5-fluoro-1,3-dimethylpyrazole) | (thiazole) | cyclopropyl | O | H | H | 295 |
| 11 | (5-fluoro-1,3-dimethylpyrazole) | (1,3,4-oxadiazole) | cyclopropyl | O | H | H | 280 |
| 12 | (5-fluoro-1,3-dimethylpyrazole) | (4-(4-chlorophenyl)thiazole) | cyclopropyl | O | H | H | 405 |
| 13 | (5-fluoro-1,3-dimethylpyrazole) | (1-methylimidazole) | cyclopropyl | O | H | H | 292 |
| 14 | (5-fluoro-1,3-dimethylpyrazole) | (3,5-dimethylisoxazole) | cyclopropyl | O | H | H | 307 |
| 15 | (5-fluoro-1,3-dimethylpyrazole) | (2-methyl-4-trifluoromethylthiazole) | cyclopropyl | O | H | H | 377 |

-continued

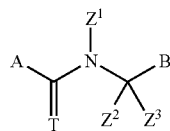

| Example N° | A | B | Z1 | T | Z2 | Z3 | M + 1 |
|---|---|---|---|---|---|---|---|
| 16 | 3-methyl-1-methyl-5-fluoro-pyrazol-4-yl | 2-methyl-4-trifluoromethyl-thiazol-5-yl | cyclopropyl | S | H | H | |
| 17 | 3-methyl-1-methyl-5-fluoro-pyrazol-4-yl | 2-(4-chlorophenyl)-4-methyl-thiazol-5-yl | cyclopropyl | O | H | H | 419 |
| 18 | 3-methyl-1-methyl-5-fluoro-pyrazol-4-yl | 3,5-dimethyl-isoxazol-4-yl | cyclopropyl | O | H | H | |
| 19 | 3-methyl-1-methyl-5-fluoro-pyrazol-4-yl | 2-trifluoromethyl-thiophen-3-yl | cyclopropyl | O | H | H | |
| 20 | 3-methyl-1-methyl-5-fluoro-pyrazol-4-yl | 5-phenyl-1,3,4-oxadiazol-2-yl | cyclopropyl | O | Me | H | |
| 21 | 3-methyl-1-methyl-5-fluoro-pyrazol-4-yl | 5-chloro-1,2,3-oxadiazol-4-yl | cyclopropyl | O | H | H | |
| 22 | 3-methyl-1-methyl-5-fluoro-pyrazol-4-yl | 2-methyl-4-trifluoromethyl-oxazol-5-yl | cyclopropyl | O | H | H | |

-continued

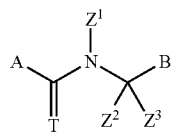

| Example N° | A | B | Z1 | T | Z2 | Z3 | M + 1 |
|---|---|---|---|---|---|---|---|
| 23 | 5-fluoro-1,3-dimethyl-1H-pyrazol-4-yl | 2-chlorothiazol-5-yl | cyclopropyl | O | Me | H | |
| 24 | 4-(difluoromethyl)-2-methylthiazol-5-yl | 1-methyl-1H-imidazol-2-yl | cyclopropyl | O | H | H | 327 |
| 25 | 4-(difluoromethyl)-2-methylthiazol-5-yl | 4-(4-chlorophenyl)thiazol-2-yl | cyclopropyl | O | H | H | 440 |
| 26 | 4-(difluoromethyl)-2-methylthiazol-5-yl | 1,2,4-oxadiazol-3-yl | cyclopropyl | O | H | H | 315 |
| 27 | 4-(difluoromethyl)-2-methylthiazol-5-yl | thiazol-4-yl | cyclopropyl | O | H | H | 330 |
| 28 | 1-methyl-4-(trifluoromethyl)-1H-pyrrol-3-yl | 4-(4-chlorophenyl)thiazol-2-yl | cyclopropyl | O | H | H | 440 |
| 29 | 1-methyl-4-(trifluoromethyl)-1H-pyrrol-3-yl | 1-methyl-1H-imidazol-2-yl | cyclopropyl | O | H | H | 327 |

-continued

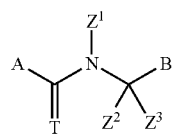

| Example N° | A | B | Z1 | T | Z2 | Z3 | M + 1 |
|---|---|---|---|---|---|---|---|
| 30 | 4-CF3-1-methyl-pyrrol-3-yl | 1,3,4-oxadiazol-2-yl | cyclopropyl | O | H | H | 315 |
| 31 | 4-CF3-1-methyl-pyrrol-3-yl | thiazol-5-yl | cyclopropyl | O | H | H | 330 |
| 32 | 4-CF3-1-methyl-pyrrol-3-yl | 3,5-dimethylisoxazol-4-yl | cyclopropyl | O | H | H | |
| 33 | 4-CF3-1-methyl-pyrrol-3-yl | 5-phenyl-1,3,4-oxadiazol-2-yl | cyclopropyl | O | Me | H | |
| 34 | 4-CF3-1-methyl-pyrrol-3-yl | 5-chloro-1,2,3-thiadiazol-4-yl | cyclopropyl | O | H | H | |
| 35 | 4-CF3-1-methyl-pyrrol-3-yl | 2-methyl-4-CF3-oxazol-5-yl | cyclopropyl | O | H | H | |
| 36 | 4-CF3-1-methyl-pyrrol-3-yl | 2-chlorothiazol-5-yl | cyclopropyl | O | Me | H | |

-continued

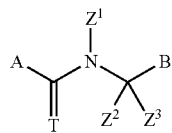

| Example N° | A | B | Z1 | T | Z2 | Z3 | M + 1 |
|---|---|---|---|---|---|---|---|
| 37 | 3-(difluoromethyl)-1-methyl-1H-pyrazol-4-yl | thiazol-4-yl | cyclopropyl | O | H | H | 313 |
| 38 | 3-(difluoromethyl)-1-methyl-1H-pyrazol-4-yl | 4-(4-chlorophenyl)thiazol-2-yl | cyclopropyl | O | H | H | 423 |
| 39 | 3-(difluoromethyl)-1-methyl-1H-pyrazol-4-yl | 2-methyl-4-(trifluoromethyl)thiazol-5-yl | cyclopropyl | O | H | H | 395 |
| 40 | 3-(difluoromethyl)-1-methyl-1H-pyrazol-4-yl | 3,5-dimethylisoxazol-4-yl | cyclopropyl | O | H | H |  |
| 41 | 3-(difluoromethyl)-1-methyl-1H-pyrazol-4-yl | 5-phenyl-1,3,4-oxadiazol-2-yl | cyclopropyl | O | Me | H |  |
| 42 | 3-(difluoromethyl)-1-methyl-1H-pyrazol-4-yl | 5-chloro-1,2,3-thiadiazol-4-yl | cyclopropyl | O | H | H |  |

-continued

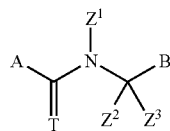

| Example N° | A | B | Z1 | T | Z2 | Z3 | M + 1 |
|---|---|---|---|---|---|---|---|
| 43 | 3-(difluoromethyl)-1-methyl-pyrazol-4-yl | 2-methyl-4-(trifluoromethyl)thiazol-5-yl | cyclopropyl | O | H | H | |
| 44 | 3-(difluoromethyl)-1-methyl-pyrazol-4-yl | 1,2,4-oxadiazol-3-yl | cyclopropyl | O | H | H | 298 |
| 45 | 3-(difluoromethyl)-1-methyl-pyrazol-4-yl | 2-(4-chlorophenyl)-4-methyl-thiazol-5-yl | cyclopropyl | O | H | H | 437 |
| 46 | 3-(difluoromethyl)-1-methyl-pyrazol-4-yl | 2-(4-chlorophenyl)-4-methyl-thiazol-5-yl | cyclopropyl | S | H | H | |
| 47 | 3-(difluoromethyl)-1-methyl-pyrazol-4-yl | 3,5-dimethyl-isoxazol-4-yl | cyclopropyl | O | H | H | 325 |
| 48 | 3-(difluoromethyl)-1-methyl-pyrazol-4-yl | 2-chloro-thiazol-5-yl | cyclopropyl | O | Me | H | |
| 49 | 2-methyl-5-(trifluoromethyl)-2H-1,2,3-triazol-4-yl | thiazol-4-yl | cyclopropyl | O | H | H | 332 |

-continued

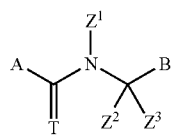

| Example N° | A | B | Z1 | T | Z2 | Z3 | M + 1 |
|---|---|---|---|---|---|---|---|
| 50 | 4-(trifluoromethyl)-2-methyl-2H-1,2,3-triazol-5-yl | 4-(4-methoxyphenyl)thiazol-2-yl | cyclopropyl | O | H | H | 442 |
| 51 | 4-(trifluoromethyl)-2-methyl-2H-1,2,3-triazol-5-yl | 1,2,4-oxadiazol-3-yl | cyclopropyl | O | H | H | 317 |
| 52 | 4-(trifluoromethyl)-2-methyl-2H-1,2,3-triazol-5-yl | 1-methyl-1H-imidazol-2-yl | cyclopropyl | O | H | H | 329 |
| 53 | 3-methoxy-1-methyl-1H-pyrazol-4-yl | 5-(4-methoxyphenyl)-4,5-dihydro-pyrrol-2-yl | cyclopropyl | O | H | H | 403 |
| 54 | 3-methoxy-1-methyl-1H-pyrazol-4-yl | thiazol-4-yl | cyclopropyl | O | H | H | 293 |
| 55 | 3-methoxy-1-methyl-1H-pyrazol-4-yl | 1,2,4-oxadiazol-3-yl | cyclopropyl | O | H | H | 278 |

-continued

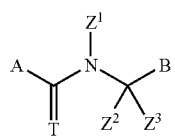

| Example N° | A | B | Z1 | T | Z2 | Z3 | M + 1 |
|---|---|---|---|---|---|---|---|
| 56 | 1-methyl-3-methoxy-pyrazol-4-yl | 1-methyl-imidazol-2-yl | cyclopropyl | O | H | H | 290 |
| 57 | 1-methyl-3-trifluoromethyl-pyrazol-4-yl | 1-methyl-imidazol-2-yl | cyclopropyl | O | H | H | 328 |
| 58 | 1-methyl-3-trifluoromethyl-pyrazol-4-yl | thiazol-4-yl | cyclopropyl | O | H | H | 331 |
| 59 | 1-methyl-3-trifluoromethyl-pyrazol-4-yl | 4-(4-methoxyphenyl)-thiazol-2-yl | cyclopropyl | O | H | H | 441 |
| 60 | 1-methyl-3-trifluoromethyl-pyrazol-4-yl | 1,2,4-oxadiazol-3-yl | cyclopropyl | O | H | H | 316 |
| 61 | 2-iodo-thiophen-3-yl | 4-(4-chlorophenyl)-thiazol-2-yl | cyclopropyl | O | H | H | 501 |

-continued

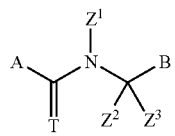

| Example N° | A | B | Z1 | T | Z2 | Z3 | M + 1 |
|---|---|---|---|---|---|---|---|
| 62 | 3-thienyl (with I) | oxadiazolyl | cyclopropyl | O | H | H | 376 |
| 63 | 3-thienyl (with I) | thiazolyl | cyclopropyl | O | H | H | 391 |
| 64 | 2-thienyl (with I) | N-methylimidazolyl | cyclopropyl | O | H | H | 388 |

The following examples illustrate in a non-limiting manner the preparation and efficacy of the compounds of formula (I) according to the invention.

PREPARATION EXAMPLE

N-cyclopropyl-N-(1,3-thiazol-4-yl-methyl)-1-methyl-3-difluoromethyl-pyrazole-4-carboxamide (Compound 37)

20 ml (0.29 mol) of cyclopropylamine was added to a solution of 4.9 g (29.0 mmol) of 4-(chloromethyl)-thiazole hydrochloride in 45 ml ethanol and 45 ml of saturated aqueous sodium hydrogen carbonate. The reaction mixture was stirred for 20 hrs at ambient temperature and extracted with ethyl acetate (3×100 ml). The combined organic layers were dried over magnesium sulphate and concentrated in vacuum. Column chromatography (gradient n-pentane/ethyl acetate) yielded 1.5 g (32% yield) of N-(1,3-thiazol-4-ylmethyl)cyclopropylamine. At ambient temperature a solution of 0.28 g (1.4 mmol) of 3-(difluoromethyl)-1-methyl-pyrazole-4-carbonyl chloride in 2 ml of tetrahydrofurane was added drop wise to a solution of 0.20 g (1.3 mmol) of N-(1,3-thiazol-4-ylmethyl)-cyclopropylamine and 0.6 ml triethylamine in 4 ml tetrahydrofurane. The reaction mixture was stirred for 16 hrs at ambient temperature and quenched with water. The watery layer was extracted three times with ethyl acetate (3×20 ml), the combined organic layers were dried over magnesium sulphate and concentrated in vacuum. Column chromatography (gradient n-pentane/ethyl acetate) yielded 0.13 mg (51% yield) of N-cyclopropyl-N-(1,3-thiazol-4-yl-methyl)-1-methyl-3-difluoromethyl-pyrazole-4-carboxamide (M+1=313).

GENERAL PREPARATION EXAMPLE

Thionation of Amide of Formula (I) on Chemspeed Apparatus

In a 13 ml Chemspeed vial is weighted 0.27 mmole of phosphorous pentasulfide ($P_2S_5$). 3 ml of a 0.18 molar solution of the amide (I) (0.54 mmole) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cardridge (2 g) and eluted twice by 8 ml of dichloromethane. The solvents are removed and the crude thioamide derivative is analyzed by LCMS and NMR. Insufficiently pure compounds are further purified by preparative LCMS.

EXAMPLE A

In Vivo Test on *Pyrenophora teres* (Barley Net Blotch)

The active ingredients tested are prepared by homogenization in a mixture of acetone/tween/DMSO, then diluted with water to obtain the desired active material concentration.

Barley plants (Express variety) in starter cups, sown on a 50/50 peat soil-pozzolana substrate and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants. Under these conditions, good (at least 70%) or total protection is observed at a dose of 500 ppm with the following compounds: 3, 17, 45 and 53.

EXAMPLE B

In Vivo Test on *Mycosphaerella graminicola* (Wheat Leaf Spot)

The active ingredients tested are prepared by homogenisation in a mixture of acetone/tween/DMSO, and then diluted with water to obtain the desired active material concentration.

Wheat plants (Scipion variety), sown on a 50/50 peat soil-pozzolana substrate in starter cups and grown at 12° C., are treated at the 1-leaf stage (10 cm tall) by spraying with the active ingredient prepared as described above.

Plants, used as controls, are treated with the mixture of acetone/tween/DMSO/water not containing the active material.

After 24 hours, the plants are contaminated by spraying them with an aqueous suspension of *Mycosphaerella graminicola* spores (500 000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 1, 12, 17, 28, 31, 39, 45, 47, 50, 53 and 59.

The invention claimed is:
1. A compound of formula (I)

(I)

wherein
$R^1$ is $C_1$-$C_8$-alkyl;
$R^2$ and $R^3$ are independently selected from the group consisting of a hydrogen atom; a halogen atom; $C_1$-$C_8$-alkyl; and $C_1$-$C_8$-halogenoalkyl comprising up to 9 halogen atoms that can be the same or different;
T is selected from the group consisting of O, S, N—$R^a$, N—$OR^a$, N—$NR^aR^b$, and N—CN;
$R^a$ and $R^b$ are independently selected from the group consisting of a hydrogen atom;
$C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl;
$C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulfonyl;
$C_1$-$C_8$-halogenoalkylsulfonyl comprising up to 9 halogen atoms that can be the same or different;
phenyl that can be substituted by up to 5 groups Q; naphthyl that can be substituted by up to 6 groups Q; phenylmethylene that can be substituted by up to 5 groups Q; phenylsulfonyl that can be substituted by up to 5 groups Q;
B represents a carbo-linked, unsaturated, 5-membered heterocyclyl group that can be substituted by up to four groups X;
$Z^1$ is selected from the group consisting of a non-substituted $C_3$-$C_7$-cycloalkyl and a $C_3$-$C_7$-cycloalkyl substituted by up to 10 atoms or groups that can be the same or different and are selected from the group consisting of a halogen atom; cyano; $C_1$-$C_8$-alkyl; $C_1$-$C_8$-halogenoalkyl comprising up to 9 halogen atoms that can be the same or different; $C_1$-$C_8$-alkoxy;
$C_1$-$C_8$-halogenoalkoxy comprising up to 9 halogen atoms that can be the same or different;
$C_1$-$C_8$alkoxycarbonyl; and $C_1$-$C_8$-halogenoalkoxycarbonyl comprising up to 9 halogen atoms that can be the same or different;
$Z^2$ and $Z^3$ are independently selected from the group consisting of a hydrogen atom; a halogen atom; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-alkynyl; cyano; nitro; $C_1$-$C_8$-alkoxy;
$C_2$-$C_8$-alkenyloxy; $C_2$-$C_8$-alkynyloxy; $C_3$-$C_7$-cycloalkyl; $C_1$-$C_8$-alkylsulphenyl; amino;
$C_1$-$C_8$-alkylamino; di-$C_1$-$C_8$-alkylamino; $C_1$-$C_8$-alkoxycarbonyl; $C_1$-$C_8$alkylcarbonyl;
$C_1$-$C_8$-alkylcarbamoyl; di-$C_1$-$C_8$-alkylcarbamoyl; and N—$C_1$-$C_8$-alkyl-$C_1$-$C_8$-alkoxycarbamoyl; or
$Z^2$ and $Z^3$ together with the carbon atom to which they are linked can form a substituted or non-substituted $C_3$-$C_7$-cycloalkyl;
each X is independently selected from the group consisting of a hydrogen atom; a halogen atom; nitro; cyano; hydroxyl; sulfanyl; amino; pentafluoro-$\lambda^6$-sulfanyl; $C_1$-$C_8$-alkyl;
$C_1$-$C_8$-halogenoalkyl comprising up to 9 halogen atoms that can be the same or different;
$C_1$-$C_8$-alkylamino; di-$C_1$-$C_8$-alkylamino; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_1$-$C_8$-alkylsulfanyl;
$C_1$-$C_8$-halogenoalkylsulfanyl comprising up to 9 halogen atoms that can be the same or different;
$C_1$-$C_8$-alkylsulfenyl; $C_1$-$C_8$-halogenoalkylsulfenyl comprising up to 9 halogen atoms that can be the same or different, $C_1$-$C_8$-alkylsulfinyl; $C_1$-$C_8$-halogenoalkylsulfinyl comprising up to 9 halogen atoms that can be the same or different; $C_1$-$C_8$-alkylsulfonyl;
$C_1$-$C_8$-halogenoalkylsulfonyl comprising up to 9 halogen atoms that can be the same or different;
$C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_2$-$C_8$-alkenyloxy; $C_2$-$C_8$-halogenoalkenyloxy comprising up to 9 halogen atoms that can be the same or different; $C_2$-$C_8$-alkynyloxy; $C_2$-$C_8$-halogenoalkynyloxy comprising up to 9 halogen atoms that can be the same or different; $C_3$-$C_7$-cycloalkyl;

$C_3$-$C_7$-cycloalkyl-$C_1$-$C_8$-alkyl; $C_3$-$C_7$-halogenocycloalkyl comprising up to 9 halogen atoms that can be the same or different; formyl; formyloxy; formylamino; carboxy; carbamoyl;

N-hydroxycarbamoyl; carbamate; (hydroxyimino)-$C_1$-$C_8$-alkyl; $C_1$-$C_8$-alkylcarbonyl;

$C_1$-$C_8$-halogenoalkylcarbonyl comprising up to 9 halogen atoms that can be the same or different;

N—$C_1$-$C_8$-alkyl-$C_1$-$C_8$-alkoxycarbamoyl; $C_1$-$C_8$-alkylcarbonyloxy;

$C_1$-$C_8$-halogenoalkylcarbonyloxy comprising up to 9 halogen atoms that can be the same or different; $C_1$-$C_8$-alkylcarbonylamino; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkoxyimino;

($C_1$-$C_8$-alkoxyimino)-$C_1$-$C_8$-alkyl; ($C_1$-$C_8$-alkenyloxyimino)-$C_1$-$C_8$-alkyl;

($C_1$-$C_8$-alkynyloxyimino)-$C_1$-$C_8$-alkyl; (benzyloxyimino)-$C_1$-$C_8$-alkyl; tri($C_1$-$C_8$-alkyl)silyl;

tri($C_1$-$C_8$-alkyl)silyl-$C_1$-$C_8$-alkyl; phenyl that can be substituted by up to 5 groups Q; benzyloxy that can be substituted by up to 5 groups Q; benzylsulfanyl that can be substituted by up to 5 groups Q; benzylamino that can be substituted by up to 5 groups Q; phenoxy that can be substituted by up to 5 groups Q; phenylamino that can be substituted by up to 5 groups Q;

phenylsulfanyl that can be substituted by up to 5 groups Q; benzyl that can be substituted by up to 5 groups Q; pyridinyl that can be substituted by up to four groups Q; and pyridinyloxy that can be substituted by up to four groups Q;

each Q is independently selected from the group consisting of a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl;

tri($C_1$-$C_8$)alkylsilyl-$C_1$-$C_8$-alkyl; $C_1$-$C_8$-alkoxyimino; and ($C_1$-$C_8$-alkoxyimino)-$C_1$-$C_8$-alkyl;

as well as salts, N-oxides, and optically active or geometric isomers thereof.

2. The compound of claim 1 wherein B is

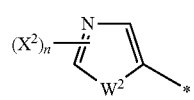

wherein:
-* represents the bond to the methylene group;
$W^2$ is selected from the group consisting of O, S, and $NX^1$;
$X^1$ is selected from the group consisting of a hydrogen atom; $C_1$-$C_8$-alkyl;
$C_1$-$C_8$-halogenoalkyl comprising up to 9 halogen atoms that can be the same or different; and
$C_1$-$C_8$-alkoxy-$C_1$-$C_8$-alkyl;
each $X^2$ is independently selected from the group consisting of a hydrogen atom; a halogen atom; cyano; $C_1$-$C_8$-alkyl; $C_1$-$C_8$-halogenoalkyl comprising up to 9 halogen atoms that can be the same or different;

$C_1$-$C_8$-alkoxy; $C_1$-$C_8$-halogenoalkoxy comprising up to 9 halogen atoms that can be the same or different; $C_3$-$C_7$-cycloalkyl; phenyl that can be substituted by up to 5 groups Q; phenoxy that can be substituted by up to 5 groups Q; benzyl that can be substituted by up to 5 groups Q; $C_1$-$C_8$-alkoxyimino; and ($C_1$-$C_8$-alkoxyimino)-$C_1$-$C_8$-alkyl; and n=1, 2 or 3.

3. The compound of claim 2 wherein $W^2$ is sulfur.

4. The compound of claim 1 wherein said compound is

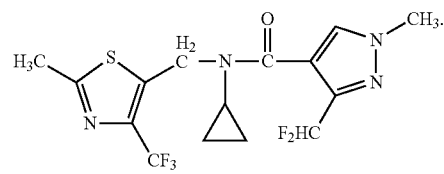

5. The compound of claim 1 wherein B is selected in the group consisting of:

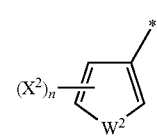

B¹

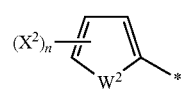

B²

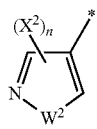

B³

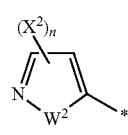

B⁴

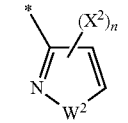

B⁵

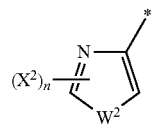

B⁶

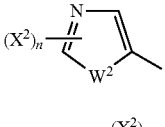

B⁷

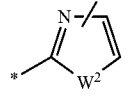

B⁸

-continued

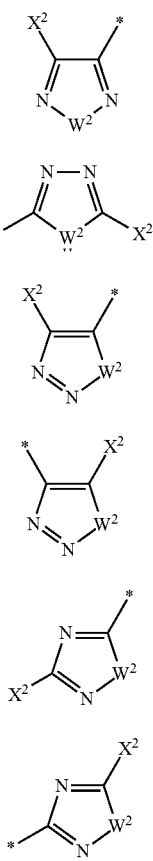

wherein:
-* represents the bond to the methylene group;
W² is selected from the group consisting of O, S, and NX¹;
X¹ is selected from the group consisting of a hydrogen atom;

$C_1$-$C_8$-alkyl; $C_1$-$C_8$-halogenoalkyl comprising up to 9 halogen atoms that can be the same or different; and $C_1$-$C_8$-alkoxy-$C_1$-$C_8$-alkyl;
each $X^2$ is independently selected from the group consisting of a hydrogen atom; a halogen atom; cyano; $C_1$-$C_8$-alkyl; $C_1$-$C_8$-halogenoalkyl comprising up to 9 halogen atoms that can be the same or different; $C_1$-$C_8$-alkoxy;
$C_1$-$C_8$-halogenoalkoxy comprising up to 9 halogen atoms that can be the same or different;
$C_3$-$C_7$-cycloalkyl; phenyl that can be substituted by up to 5 groups Q; phenoxy that can be substituted by up to 5 groups Q; benzyl that can be substituted by up to 5 groups Q;
$C_1$-$C_8$-alkoxyimino; and ($C_1$-$C_8$-alkoxyimino)-$C_1$-$C_8$-alkyl; and
n=1, 2 or 3.

6. The compound of claim 1 wherein T is selected from the group consisting of oxygen and sulfur.

7. The compound of claim 1 wherein T is oxygen.

8. The compound of claim 1 wherein $Z^1$ is cyclopropyl.

9. The compound of claim 1 wherein $Z^2$ and $Z^3$ are independently selected from the group consisting of a hydrogen atom and $C_1$-$C_8$ alkyl.

10. A fungicide composition comprising, as an active ingredient, an agronomically effective and substantially non-phytotoxic quantity of a compound of formula (I) according to claim 1 and an agriculturally acceptable support, carrier or filler.

11. A method for controlling phytopathogenic fungi of crops comprising applying an agronomically effective and substantially non-phytotoxic quantity of a compound according to claim 1 to the soil where plants grow or are capable of growing, to the leaves and/or the fruit of plants or to the seeds of plants.

12. A method for controlling phytopathogenic fungi of crops comprising applying an agronomically effective and substantially non-phytotoxic quantity of a composition according to claim 10 to the soil where plants grow or are capable of growing, to the leaves and/or the fruit of plants or to the seeds of plants.

* * * * *